United States Patent [19]

Mimaki et al.

[11] 4,054,611

[45] Oct. 18, 1977

[54] METHOD FOR THE PREPARATION OF P-ISOPROPENYL PHENOL

[75] Inventors: Kosuke Mimaki; Tsutomu Takase, both of Nagoya; Mitsuhiro Iwasa, Tokai; Tomitaka Yamamori, Nagoya, all of Japan

[73] Assignee: Mitsui Toatsu Chemicals, Incorporated, Tokyo, Japan

[21] Appl. No.: 493,661

[22] Filed: July 30, 1974

[30] Foreign Application Priority Data

Aug. 10, 1973 Japan .................................. 48-89246

[51] Int. Cl.[2] .............................................. C07C 39/06

[52] U.S. Cl. ............................. 260/626 R; 260/624 B

[58] Field of Search .......... 260/624 H, 624 A, 621 A, 260/626 R, 621 D, 627 H, 624 B, 626 T, 624 C

[56] References Cited

U.S. PATENT DOCUMENTS

| | | | |
|---|---|---|---|
| 2,736,753 | 2/1956 | Jacobs | 260/621 L |
| 3,043,882 | 7/1962 | Thompson | 260/621 D |
| 3,043,883 | 7/1962 | Thompson | 260/621 D |

FOREIGN PATENT DOCUMENTS

| | | | |
|---|---|---|---|
| 905,994 | 8/1960 | United Kingdom | 260/624 H |

OTHER PUBLICATIONS

Lutskii et al. "Chem. Abstract" vol. 64, p. 12502g (1966).

Kogan et al., "Chem. Abstract" vol. 74, p. 52733p.

*Primary Examiner*—James O. Thomas, Jr.
*Assistant Examiner*—W. B. Lone
*Attorney, Agent, or Firm*—Arnold B. Christen; Eugene Sabol

[57] ABSTRACT

Chemically stable p-isopropenyl phenol is produced in the form of a solution by contacting p-isopropenyl phenol, in the form of a gas or a liquid obtained immediately after condensation of said gas, with a polar solvent such as an alcohol, an ester, or an acid amide. The resultant solution of p-isopropenyl phenol can be used as the starting material for subsequent reaction to obtain useful compounds such as hydroquinone. Alternatively, p-isopropenyl phenol may be isolated in crystalline form by adding to the solution a poor solvent for the phenol such as water, or by cooling the solution.

8 Claims, No Drawings

METHOD FOR PREPARATION OF P-ISOPROPENYL PHENOL

BACKGROUND OF THE INVENTION

1. Field of the Invention

The present invention relates to a method for preparing p-isopropenyl phenol of high purity and, more particularly, to a method for the preparation of p-isopropenyl phenol by dissolving or collecting in an organic solvent, p-isopropenyl phenol which is obtained either by subjecting dihydroxydiphenylpropane to thermal decomposition in the presence of a basic catalyst, or by thermally treating lower polymers or oligomers of p-isopropenyl phenol in the presence or absence of a basic catalyst. The dihydroxydiphenylpropane herein described is intended to mean 2,2-(4,4'-dihydroxydiphenyl)-propane or a mixture thereof with 2-(2-hydroxyphenyl)-2-(4'-hydroxyphenyl)-propane, and is hereinafter referred to simply as bisphenol A for the sake of brevity.

2. Description of the Prior Art

It is well known in the art that thermal treatment of bisphenol A results in the formation of phenol and p-isopropenyl phenol by a decomposition reaction. Moreover, it is also known that p-isopropenyl phenol can be obtained as a by-product when diisopropylbenzene is subjected to air-oxidation and then to acid decomposition to produce a dihydric phenol. However, it is difficult to isolate highly pure p-isopropenyl phenol monomer at a high yield since the monomer polymerizes readily, especially in the molten state.

p-Isopropenyl phenol has been hithertofore isolated by the process disclosed in British Patent Specification No. 905,994 wherein a decomposition reaction mixture of bisphenol A or the mixture from which phenol has been separated is thermally treated to form p-isopropenyl phenol gas, followed by rapid cooling of the resultant p-isopropenyl phenol gas to below the melting point thereof. However, the p-isopropenyl phenol thus obtained generally contains a large amount of p-isopropenyl phenol polymers. Accordingly, it is necessary to purify by recrystallization with a solvent such as cyclohexane or n-hexane for isolation of the p-isopropenyl phenol monomer, with the result that the yield of p-isopropenyl calculated on the basis of the starting bisphenol A employed is very low. As hereinbefore described, the p-isopropenyl phenol monomer tends to polymerize readily, especially in the molten state and, even in the solid state, non-crystallized or amorphous p-isopropenyl phenol slowly polymerizes in the vicinity of room temperature, and thus it is considered to be an unstable compound.

Under these circumstances, the present inventors undertook an intensive study to provide a method for preparing p-isopropenyl phenol of high purity and at a high yield. The compound is undesirably polymerizable not only at high temperatures but also in the vicinity of room temperature. It was found that although neither can the polymerization of p-isopropenyl phenol monomer be stopped by addition of a known radical polymerization inhibitor such as an alkylphenol including 2,6-di-tert-butyl-4-methylphenol, nor stabilization of the phenol be achieved by use of a non-polar solvent such as an aliphatic hydrocarbon or the like, an organic acid, or an amine or the like, the phenol is unexpectedly maintained stable even at temperatures higher than 100° C. when dissolved in a polar solvent including an alcohol, an ester, or an acid amide. The present invention is based upon the above finding. p-Isopropenyl phenol which is dissolved in a polar solvent can be isolated from the solution by cooling or by adding thereto a poor solvent for the phenol, e.g., water. Moreover, the solution of p-isopropenyl phenol may be used as the starting material for subsequent reaction, i.e., the solution may be reacted with hydrogen peroxide in the presence of a strong acid to produce hydroquinone.

SUMMARY OF THE INVENTION

According to the present invention, there is provided a method for the preparation of p-isopropenyl phenol in the form of a stable solution at high yield by bringing p-isopropenyl phenol in the form of a gas or a liquid obtained immediately after condensation of said gas into contact with a polar solvent such as an alcohol, an ester or an acid amide. The p-isopropenyl phenol gas can be generated by (1) thermal decomposition of bisphenol A in the presence of a basic catalyst r (2) thermal decomposition of oligomers of p-isopropenyl phenol. The oligomers of p-isopropenyl phenol can be obtained by (a) condensation of a gas generated by the thermal decomposition of bisphenol A in the presence of a basic catalyst followed by removing phenol from the resultant condensation product or (b) decomposition of hydroxyhydroperxide having the formula:

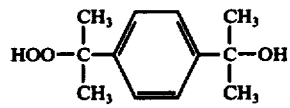

in the presence of an acid catalyst followed by removal of acetone, water and the acid catalyst from the resultant decomposition product.

DESCRIPTION OF THE PREFERRED EMBODIMENTS

As described hereinbefore, the p-isopropenyl phenol monomer tends to polymerize even under mild conditions. For example, when the monomer is maintained in the molten state at 100° C. for 10 minutes, the monomer purity is lowered to about 50%. The present invention provides a method for obtaining p-isopropenyl phenol monomer, which is unstable as such, in a stable form.

A primary feature of the present invention resides in bringing p-isopropenyl phenol generated in the form of a gas or a liquid obtained immediately after condensation of said gas into contact with a solvent. In this connection, it is preferred to contact p-isopropenyl phenol gas with a solvent prior to condensation thereof, although the condensed liquid may be dissolved in a solvent. When p-isopropenyl phenol in the form of a liquid is used, the time period tolerated before contacting the liquid with the solvent is preferred to be as short as possible, i.e., within several minutes, preferably within one minute, after condensation of the gas.

A second feature of the present invention resides in selection of the solvent to be contacted with p-isopropenyl phenol. The solvents suitable for the present invention are alcohols, esters and acid amides. By using such solvent, p-isopropenyl phenol can be obtained in a stable form. The solvents may be employed singly or in combination.

When generating p-isopropenyl phenol gas by decomposing bisphenol A thermall in the presence of a basic catalyst, the products are gaseous phenol and p-isopropenyl phenol monomer. Accordingly, in this case, the obtained solution according to the present invention is a mixed solution of p-isopropenyl phenol and phenol. When decomposing hydroxyhydroperoxide having the above-described formula in the presence of an acid catalyst, the products are p-isopropenyl phenol, acetone and water.

As described hereinbefore, condensed p-isopropenyl phenol tends to polymerize rapidly. Accordingly, oligomers of p-isopropenyl phenol can be obtained by condensation of a gas generated by thermal decomposition of bisphenol A in the presence of a basic catalyst followed by removing phenol from the resultant condensation product, or by decomposition of hydroxyhydroperoxide having the above-described formula, which is obtained as a result of oxidation of p-diisopropylbenzene, in the presence of an acid catalyst such as sulfuric acid followed by removing acetone, water and the acid catalyst from the resultant decomposition product. The term "oligomers" refers to the mixture of oligomers mainly composed of dimers, trimers, and higher polymers expressed by the following formulae and may contain to a certain extent the p-isopropenyl phenol monomer:

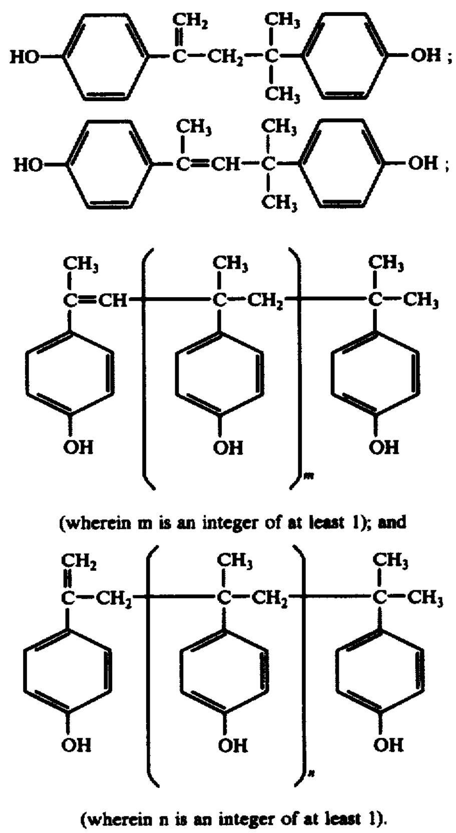

(wherein m is an integer of at least 1); and (wherein n is an integer of at least 1).

Removal of phenol from the condensation product of the gas generated by thermal decomposition of bisphenol A is easily achieved by distilling off phenol from the condensation product by heating under normal or reduced pressure, preferably under a reduced pressure of from 5 to 200 mm Hg at a temperature of from 50° to 260° C.

The basic catalysts useful in the decomposition of bisphenol A include oxides, hydroxides, alcoholates, phenolates, alkylcarboxylates, carbonates and hydrides of alkali metals, alkaline earth metals, aluminum, zinc, cadmium, and lead. The amount of the catalyst is preferably within the range of 0.01 – 5%, particularly 0.05 – 1%, by weight of bisphenol A used as starting material. When an alkali metal compound is used as catalyst, the reaction is effected at a temperature of from 150° to 260° C. Although the reaction takes place under normal pressure, it is preferable to carry out the reaction under a reduced pressure lower than 200 mm Hg.

p-Isopropenyl phenol gas can be generated by heating oligomers of p-isopropenyl phenol in the presence or absence of the above-described basic catalyst at a temperature of from 150° to 260° C. The gas generation reaction is preferably conducted under reduced pressure of from 1 to 200 mm Hg so as to efficiently produce gaseous p-isopropenyl phenol within a short period of time, although it will proceed under normal pressure.

According to the present invention, there is provided a method for the preparation of a mixed solution of p-isopropenyl phenol and phenol by bringing a mixture of p-isopropenyl phenol and phenol in the form of a gas or a liquid obtained immediately after condensation of said gas, which is generated by thermal decomposition of bisphenol A, into contact with a solvent, and a method for the preparation of solution of p-isopropenyl phenol by bringing p-isopropenyl phenol in the form of a gas or a liquid obtained immediately after condensation of said gas, which is generated by thermal decomposition of oligomers of p-isopropenyl phenol in the presence or absence of a basic catalyst, into contact with a solvent.

In practical application, it is preferred to introduce gaseous p-isopropenyl phenol into a gas-absorbing tower for contact with the solvent to obtain p-isopropenyl phenol in solution. Alternatively, the condensed p-isopropenyl phenol may be contacted with the solvent while being conducted to a receiver or may be introduced into a receiver in which the solvent has been previously charged. Also, a solvent which has a boiling point similar to that of p-isopropenyl phenol may be added to the starting bisphenol A or oligomers of p-isopropenyl phenol in order to distill out the solvent and p-isopropenyl phenol at the same time to obtain directly p-isopropenyl phenol in the form of a solution. The methods for contact of p-isopropenyl phenol with a solvent described above are shown by way of illustration only.

As described hereinbefore, in order to generate p-isopropenyl phenol gas by treating bisphenol A or oligomers of p-isopropenyl phenol at high temperatures ranging from 150° C. to 260° C. in the presence or absence of a basic catalyst, it is preferred for smooth and effective operation to carry out the generation reaction under reduced pressure below 200 mm Hg. Accordingly, a solvent to be contacted with the thus generated p-isopropenyl phenol gas desirably has a boiling point higher than room temperature (30° C.) under a reduced pressure below 200 mm Hg, preferably below 50 mm Hg. That is, the boiling point of a solvent under normal pressure is preferred to be above 100° C., particularly 150° C. or higher. Furthermore, when the solvent used has a melting point higher than normal temperature, contact of the p-isopropenyl phenol monomer with the solvent must be effected undesirably at high temperatures, so that even if a solvent of the types described above is employed for contacting purposes polymerization of p-isopropenyl phenol will take place. Accordingly, the melting point of the solvent to be used is preferably lower than 50° C.

Alcohols useful for the purpose of the present invention include, for example, a monohydric alcohol expressed by the formula

ROH (wherein R represents alkyl containing from 5 to 14 carbon atoms, cycloalkyl containing from 5 to 6 carbon atoms or aralkyl containing from 7 to 10 carbon atoms); a dihydric alcohol or a derivative thereof expressed either by the formula $$HO(\overset{R_1}{\overset{|}{C}H}-\overset{R_2}{\overset{|}{C}H}O)_mR_3$$

(wherein $R_1$ and $R_2$ are independently hydrogen or alkyl containing from 1 to 4 carbon atoms, $R_3$ is hyrogen, alkyl containing from 1 to 4 carbons or acetyl, and *m* is an integer of from 1 to 4) or by the formula $$HOC_nH_{2n}OR_4$$

(wherein $R_4$ is hydrogen, alkyl containing from 1 to 4 carbon atoms or acetyl and n is an integer of from 3 to 6); or a trihydric alcohol or a derivative thereof expressed by the formula $$HOC_3H_5(OR_5)_2$$

(wherein $R_5$ is hydrogen, alkyl containing from 1 to 4 carbon atoms or acetyl).

Examples of esters useful for the present invention include compounds represented by the formula $$R_6COOR_7$$

(wherein $R_6$ and $R_7$ are independently alkyl containing from 4 to 8 carbon atoms or cycloalkyl containing from 5 to 7 carbon atoms and the total number of carbon atoms contained in one molecule of the ester ranges from 6 to 20).

Examples of an acid amide useful for the present invention include compounds expressed by the formula $$R_8-\underset{\underset{O}{\|}}{C}-N\begin{matrix} R_9 \\ R_{9'} \end{matrix}$$

(wherein $R_8$, $R_9$ aand $R_{9'}$ are respectively hydrogen or alkyl containing from 1 to 4 carbon atoms).

More particularly, examples of solvents suitable for the purpose of the present invention include: monohydric alcohols such s n-hexanol, n-heptanol, n-octanol, 2-octanol, 2-ethylhexanol, nonanol, n-decanol, undecanol, n-dodecanol, cyclohexanol, 2-methylcyclohexanol, benzyl alcohol and the like; polyhydric alcohols such as ethylene glycol, propylene glycol, diethylene glycol, triethylene glycol, dipropylene glycol, 1,6-hexanediol, 2-methyl-2,4-pentanediol, 1,4-butanediol, 1,3-butanediol, glycerine and the like; derivatives of polyhydric alcohols such as ethylene glycol monethyl ether, ethylene glycol monobutyl ether, ethylene glycol monoacetate, diethylene glycol monobutyl ether, propylene glycol monobutyl ether and the like; esters such as n-amyl acetate, isoamyl acetate, cyclohexyl acetate, 2-ethylhexyl acetate, isoamyl propionate, n-butyl butyrate, isoamyl butyrate and the like; and acid amides such as N,N-dimethyl-formamide, acetamide and the like. These solvents may be employed singly or in combination.

The mixing ratio of solvent to p-isopropenyl phenol is not critical, so long as the solvent is used in an amount sufficient to dissolve the p-isopropenyl phenol therein. In general, the solvent is employed in an amount, by weight, equivalent to or greater than the formed p-isopropenyl phenol.

The reasons why p-isopropenyl phenol monomer is stabilized in a solvent according to the present invention are not known at present. However, it is assumed that although p-isopropenyl phenol appears to polymerize at room temperature or higher temperatures through a catio polymerization reaction, a polar solvent acts to suppress by solvation the reaction of the monomer with carbonium ions which are produced as a polymerization intermediate during the cation polymerization. This assumption is supported by the fact that a polar solvent such as an alcohol, an ester or an acid amide as described above is remarkably effective in stabilization of the monomer, but little effect is obtained with a nonpolar solvent or a radical polymerization inhibitor.

In order to isolate p-isopropenyl phenol from the solution obtained according to the present invention, the solution is cooled to crystallize the p-isopropenyl phenol, followed by separation of the crystallized phenol from the solution. Alternatively, a poor solvent for the phenol may be added to the solution for crystallization. In the first method, it is preferred to use a solvent which varies greatly in solubility depending upon temperature. Examples of such a solvent are aliphatic monohydric alcohols. On the other hand, in the latter method a water-soluble polar solvent is preferably employed, e.g., a dihydric alcohol such as ethylene glycol, diethylene glycol or propylene glycol, so that water can be used as the poor solvent for crystallization.

Furthermore, the p-isopropenyl phenol solution as such may be employed as the starting material for further reaction, if desired. For example, the solution can be subjected to reaction with hydrogen peroxide in the presence of a strong acid to obtain hydroquinone.

p-Isopropenyl phenol which is obtained in accordance with the present invention is useful not only as an intermediate of chemical products, but also as a starting material for thermoplastic and thermosetting resins.

The present invention will be particularly illustrated in the following examples wherein parts and percentages are by weight and wherein the component analyses were effected in accordance with gas chromatography.

EXAMPLES 1-12

500 parts of a dephenolized decomposition product of bisphenol A which contained 8% of p-isopropenyl phenol monomer, 85% of the linear dimer of p-isopropenyl phenol and 7% of oligomers including the trimer was introduced into a distillation kettle and slowly heated under a reduced pressure below 500 mm Hg. When the temperature within the kettle reached 150° C., distillation of p-isopropenyl phenol began. The kettle was further slowly heated until the temperature within the kettle was raised finally to 230° C. The distillation kettle was provided with a distillation column and was also provided, midway between the head of the distillation column and a downwardly slanting cooling tube, with a packed column equipped with an inlet for supplying solvent. 1000 parts of n-octanol was continuously charged from the inlet to allow the generated p-isopropenyl phenol gas to be absorbed therein. The resultant solution was cooled by means of a cooler and collected in a receiver. There remained only 20 - 50 parts of a tar-like tacky material in the kettle. The total amount of distillate, content (%) of p-isopropenyl phenol monomer in the distillate and monomer yield are shown in Table 1.

The above procedure was repeated with each of the solvents listed in Table 1 under Examples 2-10.

For comparative purposes, the above procedure was repeated without use of solvent and with use of n-decane as solvent. The test results are also shown in the Table under Comparative Examples 11 and 12.

Table 1

| Example | Solvent | Total Amount of Distillate* (Parts by weight) | Content of Monomer** (%) | Yield of Monomer*** (%) |
|---|---|---|---|---|
| 1 | n-octanol | 476 | 99.8 | 95.0 |
| 2 | diethylene glycol | 486 | 99.5 | 96.8 |
| 3 | propylene glycol | 478 | 98.7 | 94.4 |
| 4 | benzyl alcohol | 471 | 98.8 | 93.0 |
| 5 | cyclohexanol | 471 | 97.2 | 91.6 |
| 6 | glycerine | 481 | 99.2 | 95.4 |
| 7 | 1,3-butanediol | 484 | 98.9 | 95.0 |
| 8 | diethylene glycol monobutyl ether | 479 | 98.2 | 94.0 |
| 9 | dimethyl-formamide | 470 | 99.6 | 93.6 |
| 10 | 2-ethylhexyl acetate | 474 | 99.2 | 94.0 |
| Comparative Examples | | | | |
| 11 | Nil | 478 | 57.5 | 55.0 |
| 12 | n-decane | 460 | 62.8 | 57.8 |

Notes on Table 1:
*Not including solvent
**Ratio of p-isopropenyl phenol monomer to total distillate.
***Yield of Monomer = $\frac{\text{(Content of Monomer)} \times \text{(Total Amount of Distillate)}}{\text{Amount of decomposition product of bisphenol A charged}}$ tained 100 parts of a non-volatile heating medium and was maintained at 210° C. for assuring a smooth thermal treatment of the oligomers. p-Isopropenyl phenol gas generated was absorbed by means of 2-ethylhexanol in an absorber to obtain 4365 parts of a solution which contained 1339 parts of p-isopropenyl phenol monomer, 117 parts of p-isopropenyl phenol oligomers and the balance of 2-ethylhexanol.

EXAMPLES 15-26

100 parts of p-isopropenyl phenol monomer having a purity of 99.8% was dissolved in 300 parts of each of the solvents listed in the following Table 2 under Examples 15-18. Each solution was allowed to stand at 60° C. for 24 hours, after which the oligomers formed during this time were measured. The amounts of oligomers formed are shown in Table 2.

EXAMPLE 13

288 parts of bisphenol A and 0.46 part of powdered sodium hydroxide were introduced into a distilling kettle and heated under a reduced pressure of 10 mm Hg. The distillation kettle was provided with a distillation column and was also provided with a packed column equipped with an inlet for supplying solvent as in Examples 1-10. Distillation of the decomposition product commenced when the temperature within the kettle reached 190° C. Upon commencement of the distillation, ethylene glycol was continuously charged from the inlet to allow the generated gaseous p-isopropenyl phenol to be absorbed therein. The charging rate was controlled to about twice that of the distillation rate of the product. The distilled product was absorbed and dissolved in the solvent within the packed column. The ethylene glycol solution of p-isopropenyl phenol and phenol flowed down through the cooling tube and collected in a receiver, cooled with ice-water, to provide 656 parts of the solution which contained 450 parts of ethylene glycol, 88 parts of phenol, 116 parts of p-isopropenyl phenol monomer and 2 parts of p-isopropenyl phenol oligomers.

EXAMPLE 14

1500 parts of a mixture composed of monomer and oligomers of p-isopropenyl phenol, maintained at 120° C., was continuously fed into a reactor equipped with a nitrogen-blowing tube for 7 hours under a reduced pressure of 20 mm Hg. The reactor previously con- For comparative purpose, the above process was repeated without use of solvent and with use of nitrobenzene, dimethylsulfoxide, dioxane, benzene, phenol, n-octane and monochlorobenzene as solvent. The test results are also shown in the Table under Examples 19-26.

Table 2

| Example | Solvent | The amount of oligomers formed (%) |
|---|---|---|
| 15 | n-octanol | 4.85 |
| 16 | n-dodecanol | 6.28 |
| 17 | ethylene glycol | 5.03 |
| 18 | propylene glycol | 6.02 |
| Comparative Example | | |
| 19 | Nil | 28.20 |
| 20 | nitrobenzene | 15.66 |
| 21 | dimethylsulfoxide | 11.81 |
| 22 | dioane | 13.98 |
| 23 | benzene | 21.73 |
| 24 | phenol | 24.82 |
| 25 | n-octane | 22.83 |
| 26 | monochlorbenzene | 20.75 |

What is claimed is:

1. A method for the recovery of p-isopropenyl phenol in the form of a stable solution which comprises contacting p-isopropenyl phenol, in the form of a gas or of a liquid obtained immediately after condensation of said gas, said p-isopropenyl phenol gas being generated by thermal decomposition at a temperature of from 150° to 260° C. and at a pressure up to normal pressure of:

a. bisphenol A in the presence of a catalytic amount of a base catalyst; or b. oligomers of p-isopropenyl phenol in the absence of catalyst or in the presence of a catalytic amount of a basic catalyst, directly with a solvent selected from the group consisting of: a monohydric alcohol expressed by the formula

ROH wherein R is alkyl containing from 5 to 14 carbon atoms, cycloalkyl containing from 5 to 6 carbon atoms, or aralkyl containing from 7 to 10 carbon atoms; a dihydric alcohol or derivative thereof expressed by the formula

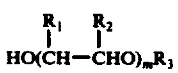

wherein $R_1$ and $R_2$ are independently hydrogen or alkyl containing from 1 to 4 carbon atoms, $R_3$ is hydrogen, alkyl containing from 1 to 4 carbon atoms or acetyl and *m* is an integer of from 1 to 4; a dihydric alcohol or derivative thereof expressed by the formula $HOC_nH_{2n}OR_4$ wherein $R_4$ is hydrogen, alkyl containing from 1 to 4 carbon atoms or acetyl, and *n* is an integer of from 3 to 6; and a trihydric alcohol or derivative thereof expressed by the formula $HOC_3H_5(OR_5)_2$ wherein $R_5$ is hydrogen, alkyl containing from 1 to 4 carbon atoms or acetyl; an ester expressed by the formula $R_6COOR_7$ wherein $R_6$ and $R_7$ are independently alkyl or cycloalkyl and the total number of carbon atoms in one molecule of the ester is within the range of from 6 to 20; and an acid amide expressed by the formula

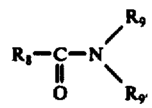

wherein $R_8$, $R_9$ and $R_{9'}$ are independently hydrogen or alkyl containing from 1 to 4 carbon atoms, and collecting said p-isopropenyl phenol in the form of a solution in said solvent.

2. The method according to claim 10 wherein said p-isopropenyl phenol gas is generated by thermal decomposition of bisphenol A at a temperature of from 150° to 260° C. and at a pressure up to normal pressure in the presence of a basic catalyst.

3. The method according to claim 10 wherein said p-isopropenyl phenol gas is generated by thermal decomposition of oligomers of p-isopropenyl phenol at a temperature of from 150° to 260° C. and at a pressure up to normal pressure, said oligomers having been obtained by condensation of a gas generated by thermal decomposition of bisphenol A at a temperature of from 150° to 260° C. and at a pressure up to normal pressure in the presence of a basic catalyst followed by removing phenol from the resultant condensation product.

4. The method according to claim 10 wherein said p-isopropenyl phenol gas is generated by thermal decomposition of oligomers of p-isopropenyl phenol at a temperature of from 150° to 260° C. and at a pressure up to normal pressure, said oligomers having been obtained by decomposition of hydroxyhydroperoxide having the formula

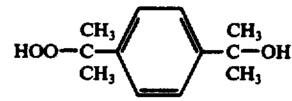

in the presence of an acid catalyst followed by removing acetone, water and the acid catalyst from the resultant decomposition product.

5. The method according to claim 1 wherein said solvent is a polar solvent having a boiling point higher than room temperature under a reduced pressure below 200 mm Hg and above 100° C. at normal pressure and a melting point lower than 50° C.

6. The method according to claim 1 wherein said solvent is an alcohol selected from said monohydric, dihydric and polyhydric alcohols.

7. The method according to claim 1 wherein said solvent is said ester.

8. The method according to claim 1 wherein said solvent is said acid amide.

* * * * *